United States Patent [19]

Rovnyak

[11] 4,127,667
[45] Nov. 28, 1978

[54] SUBSTITUTED THIOPYRANO(4,3-b)PYRANS

[75] Inventor: George C. Rovnyak, Hopewell, N.J.

[73] Assignee: E. R. Squibb & Sons, Inc., Princeton, N.J.

[21] Appl. No.: 893,722

[22] Filed: Apr. 5, 1978

[51] Int. Cl.$^2$ .................. A61K 31/335; A61K 31/38; C07D 493/02; C07D 497/02

[52] U.S. Cl. .................... 424/275; 424/279; 542/449

[58] Field of Search ............... 424/275, 279; 542/449; 260/327 R, 340.2

[56] References Cited

U.S. PATENT DOCUMENTS

3,979,381  9/1976  Rovnyak .................... 542/449

OTHER PUBLICATIONS

Linde et al, Chemical Abstracts, vol. 67, Abst. No. 32610y (1967).
Biglino et al, Chemical Abstracts, vol. 72, Abst. No. 100558t (1970).
Chemical Abstracts, vol. 84, Subject Index p. 5150CS (1976).
Tan et al, Chemical Abstracts, vol. 86, Abst. No. 106428m (1977).

*Primary Examiner*—John D. Randolph
*Attorney, Agent, or Firm*—Lawrence S. Levinson; Merle J. Smith; Burton Rodney

[57] ABSTRACT

3,4,7,8-Tetrahydro-2H,5H-thiopyrano[4,3-b]pyrans of the structure

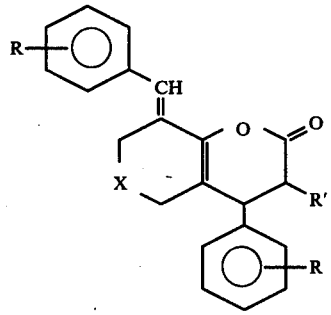

are provided wherein X is O, S or SO$_2$, R is hydrogen, halogen, lower alkyl, lower alkoxy, cyano or trifluoromethyl, and R' is carbethoxy, carboxy, alkali metal carboxylate and cyano. These compounds are useful as antiinflammatory agents and anti-hypertensive agents.

12 Claims, No Drawings

SUBSTITUTED THIOPYRANO(4,3-B)PYRANS

FIELD OF THE INVENTION

The present invention relates to substituted thiopyrano[4,3-b]pyrans, and more particularly to 3,4,7,8-tetrahydro-2H,5H-thiopyrano[4,3-b]pyrans which are useful as antiinflammatory agents and anti-hypertensive agents.

DESCRIPTION OF THE INVENTION

The 3,4,7,8-tetrahydro-2H,5H-thiopyrano[4,3-b]pyrans of the invention have the general structure

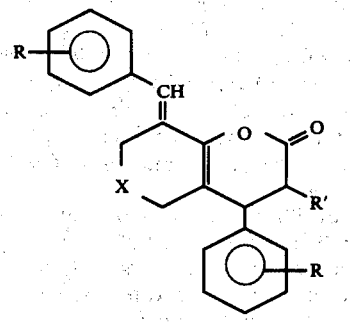

wherein X is O, S or $SO_2$, R is hydrogen, halogen, lower alkyl, lower alkoxy, cyano or trifluoromethyl, and R' is carbethoxy, carboxy, alkali metal carboxylate and cyano.

Preferred are those compounds of formula I wherein X is S, R is hydrogen, lower alkyl or trifluoromethyl and R' is carbethoxy or cyano.

The terms "alkyl" and "alkoxy", as used throughout the specification (individually or as part of a larger group), refer to groups having 1 to 8 carbon atoms. Alkyl and alkoxy groups having 1 to 3 carbon atoms are preferred.

The term "halogen", as used throughout the specification, refers to fluorine, chlorine, bromine and iodine; fluorine and chlorine are preferred.

The term "alkali metal carboxylate" refers to sodium or potassium linked to a carboxyl group.

Compounds of formula I are prepared by reacting an unsaturated ketone of formula II with an alkali metal salt of a reactive methylene compound of formula III in a mole ratio of II:III from 1:1 to 1:2, and preferably in a ratio of II:III from 1:1 to 1:1.2, in an alcoholic solvent at reflux temperature for from 1 to 12 hours, preferably for from 2 to 4 hours. Sodium ethoxide in ethanol is a convenient base-solvent system, although other alkali metal counter ions and other alcoholic solvents are compatible.

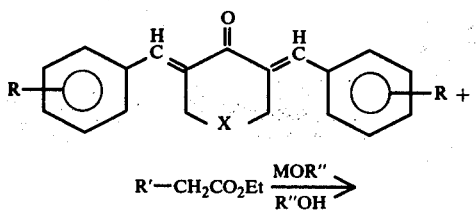

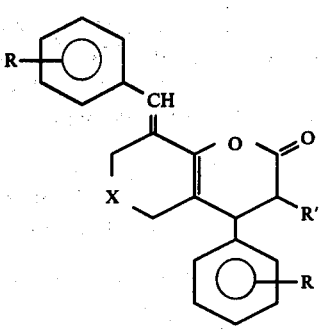

M = Na, K, Li
R" = 1-5 carbon alkyl

Unsaturated ketones of formula II are prepared as described in J.A.C.S., 79, 156 (1957).

The compounds of the invention have antiinflammatory activity as measured by the mouse active arthus (MAA) test and are useful as antiinflammatory agents and are effective in the prevention and inhibition of granuloma tissue formation in warm blooded animals, and may be used, for example, in a manner similar to phenylbutazone or indomethacin. They may be used to decrease joint swelling, tenderness, pain and stiffness in mammalian species, such as dogs and monkeys, e.g., in conditions such as rheumatoid arthritis.

The compounds of the invention also have antihypertensive activity as measured by the rat spontaneous hypertensive model and thus may be used in the treatment of hypertension.

Compounds of formula I or a physiologically acceptable acid-addition salt thereof may be compounded for such use according to accepted pharmaceutical practice in oral dosage forms such as tablets, capsules, elixirs or powders or in injectable form for administration of about 100 mg to 2 gm per day, preferably 100 mg to 1 gm per day in two to four divided doses.

The following examples further illustrate and represent preferred embodiments of the invention. All temperatures are expressed in degrees Centigrade.

EXAMPLE 1

3,4,7,8-Tetrahydro-2-oxo-4-phenyl-8-(phenylmethylene)-2H,5H-thiopyrano[4,3-b]pyran-3-carboxylic acid, ethyl ester To an ethanolic solution of sodium ethoxide [prepared from 555 mg (24 mg atom) of sodium in 50 ml of ethanol] is added diethyl malonate (3.52 g, 22 mmole) in 50 ml of absolute ethanol. After heating at reflux temperature for 2 hours, tetrahydro-3,5-bis(phenylmethylene)-4H-thiopyran-4-one (5.84 g, 20 mmole) is added. The resulting solution is then heated at reflux temperature for 2 hours.

Solvent is removed in vacuo and the residue, dissolved in $CHCl_3$, is washed with dilute aqueous HCl and $H_2O$. The organic phase is dried ($CaCl_2$), concentrated in vacuo and the residual oil is triturated with warm ether. The solid (5.5 g) obtained is recrystallized from $CHCl_3$/hexane to give 3.3 g (40%) (m.p. 114°–118°) of product.

EXAMPLE 2

3,4,7,8-Tetrahydro-4-(2-methylphenyl)-8-[(2-methylphenyl)methylene]-2-oxo-2H,5H-thiopyrano[4,3-b]pyran-3-carboxylic acid, ethyl ester A. Tetrahydro-3,5-bis[(2-methylphenyl)methylene]-4H-thiopyran-4-one Tetrahydro-4H-thiopyran-4-one (9.3 g, 0.08 mole) and o-tolualdehyde (25 g, 0.20 mole) are dissolved in 60 ml of ethanol and treated with concentrated hydrochloric acid (6 ml). After heating at reflux temperature for 4 hours, the mixture is cooled and product is collected by filtration. The combined filtrate and washings (ethanol) are concentrated to the original volume and additional concentrated hydrochloric acid (4 ml) is added and the mixture is refluxed for 4 hours. This procedure is repeated 3 times. The combined crude material (23 g) is recrystallized from chloroform/ethanol/H$_2$O to give 22.5 g (88%) of product, m.p. 123°–125°.

B. 3,4,7,8-Tetrahydro-4-(2-methylphenyl)-8-[(2-methylphenyl)methylene]-2-oxo-2H,5H-thiopyrano[4,3-b]pyran-3-carboxylic acid, ethyl ester The reaction is performed as described for the compound of Example 1, except that tetrahydro-3,5-bis[(2-methylphenyl)methylene]-4H-thiopyran-4-one is used. Thus, from 3.2 g (10 mmole) of tetrahydro-3,5-bis[(2-methylphenyl)methylene]-4H-thiopyran-4-one, there is obtained 3.0 g (69%) of product (trituration of crude oily product with hexane), m.p. 169°–173°.

EXAMPLE 3

3,4,7,8-Tetrahydro-2-oxo-4-[3-(trifluoromethyl)phenyl]-8-[[3-(trifluoromethyl)phenyl]methylene]-2H,5H-thiopyrano-[4,3-b]pyran-3-carboxylic acid, ethyl ester A. Tetrahydro-3,5-bis[[3-(trifluoromethyl)phenyl]methylene]-4H-thiopyran-4-one The procedure as described in Example 2, part A, above is employed. Thus, from 23.2 g (0.2 mole) of tetrahydro-4H-thiopyran-4-one and 76.6 g (0.44 mole) of 3-trifluoromethylbenzaldehyde, there is obtained 53.9 g (63%) of product, m.p. 113.5°–116°, recrystallized from CHCl$_3$/EtOH (1:5).

B. 3,4,7,8-Tetrahydro-2-oxo-4-[3-(trifluoromethyl)phenyl]-8-[[3-trifluoromethyl)phenyl]methylene]-2H,5H-thiopyrano[4,3-b]pyran-3-carboxylic acid, ethyl ester The reaction is performed as described for the compound of Example 1, except that tetrahydro-3,5-bis[[3-(trifluoromethyl)phenyl]methylene]-4H-thiopyran-4-one is used. Thus, from 4.28 g (10 mmole) of tetrahydro-3,5-bis[[3-(trifluoromethyl)phenyl]methylene]-4H-thiopyran-4-one, there is obtained 3.8 g (70%) of product (crystallized from EtOH/H$_2$O), m.p. 153°–157°.

EXAMPLE 4

3,4,7,8-Tetrahydro-2-oxo-4-phenyl-8-(phenylmethylene)-2H,5H-thiopyrano[4,3-b]pyran-3-carbonitrile To a solution of NaOEt (from 555 mg, 92 mg atom Na in absolute EtOH) in 100 ml of absolute EtOH is added ethyl cyanoacetate (2.44 g, 22 mmole) dissolved in 50 ml of absolute EtOH. This is heated at reflux temperature for 2 hours, cooled slightly and tetrahydro-3,5-bis(phenylmethylene)-4H-thiopyran-4-one (5.84 g, 20 mmole) is added at once. The mixture quickly turns orange-red for ca. 10 minutes, changing to yellow (yellow solids in orange-red solution) as heating is continued for 2 hours.

The cooled solution is filtered and the solids are washed with a small amount of EtOH to give 3.0 g of crude product. This is dissolved in CHCl$_3$ and washed with 10% HCl and H$_2$O, dried (CaCl$_2$) and concentrated in vacuo. The residue, upon trituration with hot hexane, cooling and filtration affords 2.4 g (33%) of product, m.p. 140°–143°.

EXAMPLES 5 TO 30

Following the procedure of Example 1, except substituting for tetrahydro-3,5-bis(phenylmethylene)-4H-thiopyran-4-one, the compound shown in Column I of Table I set out below, and substituting for diethyl malonate, the compound shown in Column II, the product shown in Column III is obtained.

In cases where R' (Table I, Column II) is COOH, COONa or COOK, two equivalents of base are employed to form the dianion. The product is isolated as the free acid (COOH) and the sodium (Na) or potassium (K) salt is made by adding one equivalent of the appropriate alkali metal alkoxide in an alcoholic solvent and removing the solvent.

TABLE I

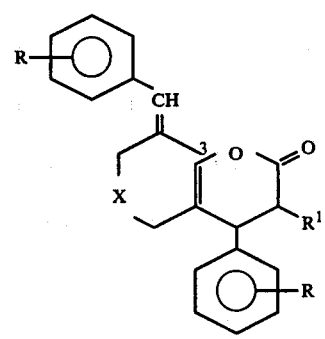

Column II
R$^1$—CH$_2$CO$_2$C$_2$H$_5$

| Ex. No. | R(position) | X | R$^1$ | R(position) | X | R$^1$ |
|---|---|---|---|---|---|---|
| 5. | Cl (4) | O | CO$_2$C$_2$H$_5$ | as per Column I | | as per Column II |
| 6. | C$_2$H$_5$ (4) | O | COOH | | | |
| 7. | C$_2$H$_5$O (4) | O | CO$_2$Na | | | |
| 8. | CN (4) | O | COOH | | | |
| 9. | CF$_3$ (2) | O | CN | | | |

TABLE I-continued

| | Column I | | | Column III | | |
|---|---|---|---|---|---|---|
| | | | | Column II | | |
| | | | | $R^1$—$CH_2CO_2C_2H_5$ | | |
| Ex. No. | R(position) | X | $R^1$ | R(position) | X | $R^1$ |
| 10. | H (3) | O | $CO_2K$ | | | |
| 11. | Br (3) | O | $CO_2C_2H_5$ | | | |
| 12. | $CF_3$ (4) | O | COOH | | | |
| 13. | H | O | CN | | | |
| 14. | $C_3H_7$ (4) | O | $CO_2Na$ | | | |
| 15. | CN (4) | O | CN | | | |
| 16. | Cl (4) | S | $CO_2C_2H_5$ | | | |
| 17. | $C_2H_5$ (4) | S | COOH | | | |
| 18. | $C_2H_5O$ (3) | S | $CO_2Na$ | | | |
| 19. | CN (4) | S | COOH | | | |
| 20. | $CF_3$ (2) | S | CN | | | |
| 21. | H (3) | S | $CO_2K$ | | | |
| 22. | Br (3) | S | $CO_2C_2H_5$ | | | |
| 23. | $CF_3$ (4) | S | COOH | | | |
| 24. | Cl (4) | $SO_2$ | $CO_2C_2H_5$ | | | |
| 25. | $C_2H_5$ (4) | $SO_2$ | COOH | | | |
| 26. | $C_2H_5O$ (3) | $SO_2$ | $CO_2Na$ | | | |
| 27. | CN (4) | $SO_2$ | COOH | | | |
| 28. | $CF_3$ (2) | $SO_2$ | CN | | | |
| 29. | H (3) | $SO_2$ | $CO_2K$ | | | |
| 30. | Br (3) | $SO_2$ | $CO_2C_2H_5$ | | | |

What is claimed is:

1. A compound of the structure

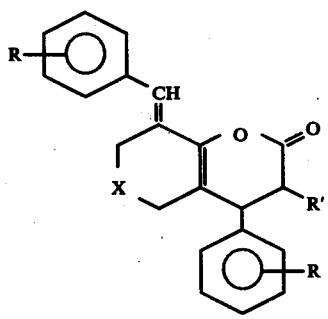

wherein X is O, S or $SO_2$, R is H, halo, alkyl, alkoxy, cyano or trifluoromethyl and R' is carbethoxy, carboxy, alkali metal carboxylate or cyano, and physiologically acceptable salts thereof.

2. The compound of claim 1 wherein X is S.
3. The compound of claim 1 wherein X is O or $SO_2$.
4. The compound of claim 1 wherein R is hydrogen, lower alkyl or trifluoromethyl.
5. The compound of claim 1 wherein R' is carbethoxy or cyano.
6. The compound of claim 1 having the name 3,4,7,8-tetrahydro-2-oxo-4-phenyl-8-(phenylmethylene)-2H,5H-thiopyrano[4,3-b]pyran-3-carboxylic acid, ethyl ester.
7. The compound of claim 1 having the name 3,4,7,8-tetrahydro-4-(2-methylphenyl)-8-[(2-methylphenyl)methylene]-2-oxo-2H,5H-thiopyrano[4,3-b]pyran-3-carboxylic acid, ethyl ester.
8. The compound of claim 1 having the name 3,4,7,8-tetrahydro-2-oxo-4-[3-(trifluoromethyl)phenyl]-8-[[(3-trifluoromethyl)phenyl]methylene]-2H,5H-thiopyrano[4,3-b]pyran-3-carboxylic acid, ethyl ester.
9. The compound of claim 1 having the name 3,4,7,8-tetrahydro-2-oxo-4-phenyl-8-(phenylmethylene)-2H,5H-thiopyrano[4,3-b]pyran-3-carbonitrile.
10. A pharmaceutical composition comprising a compound as defined in claim 1 and a pharmaceutically acceptable carrier therefor.
11. A method for treating an inflammatory condition in mammals, which comprises administering a therapeutically effective amount of a compound as defined in claim 1.
12. A method for treating hypertension in mammals, which comprises administering a therapeutically effective amount of a compound as defined in claim 1.

UNITED STATES PATENT AND TRADEMARK OFFICE
CERTIFICATE OF CORRECTION

PATENT NO. : 4,127,667

DATED : November 28, 1978

INVENTOR(S) : George C. Rovnyak

It is certified that error appears in the above–identified patent and that said Letters Patent are hereby corrected as shown below:

Column 1, before the first structure insert --I--.
Columns 4 and 6, Table I, Column III, in the structures delete "3".
Column 3, Table I, Example 7, Column I, "$C_2H_5O(4)$" should read --$C_2H_5O(3)$--.
Column 6, Table I, Column III, the column headings should read as follows:

$$-- \underbrace{R(position) \quad X}_{\text{as per Column I}} \quad \underbrace{R^1}_{\text{as per Column II}} --$$

Signed and Sealed this

Twenty-seventh Day of March 1979

[SEAL]

Attest:

RUTH C. MASON
Attesting Officer

DONALD W. BANNER
Commissioner of Patents and Trademarks